Aug. 5, 1969 D. L. ARMSTRONG Plant Pat. 2,914
ROSE PLANT
Filed Dec. 13, 1967
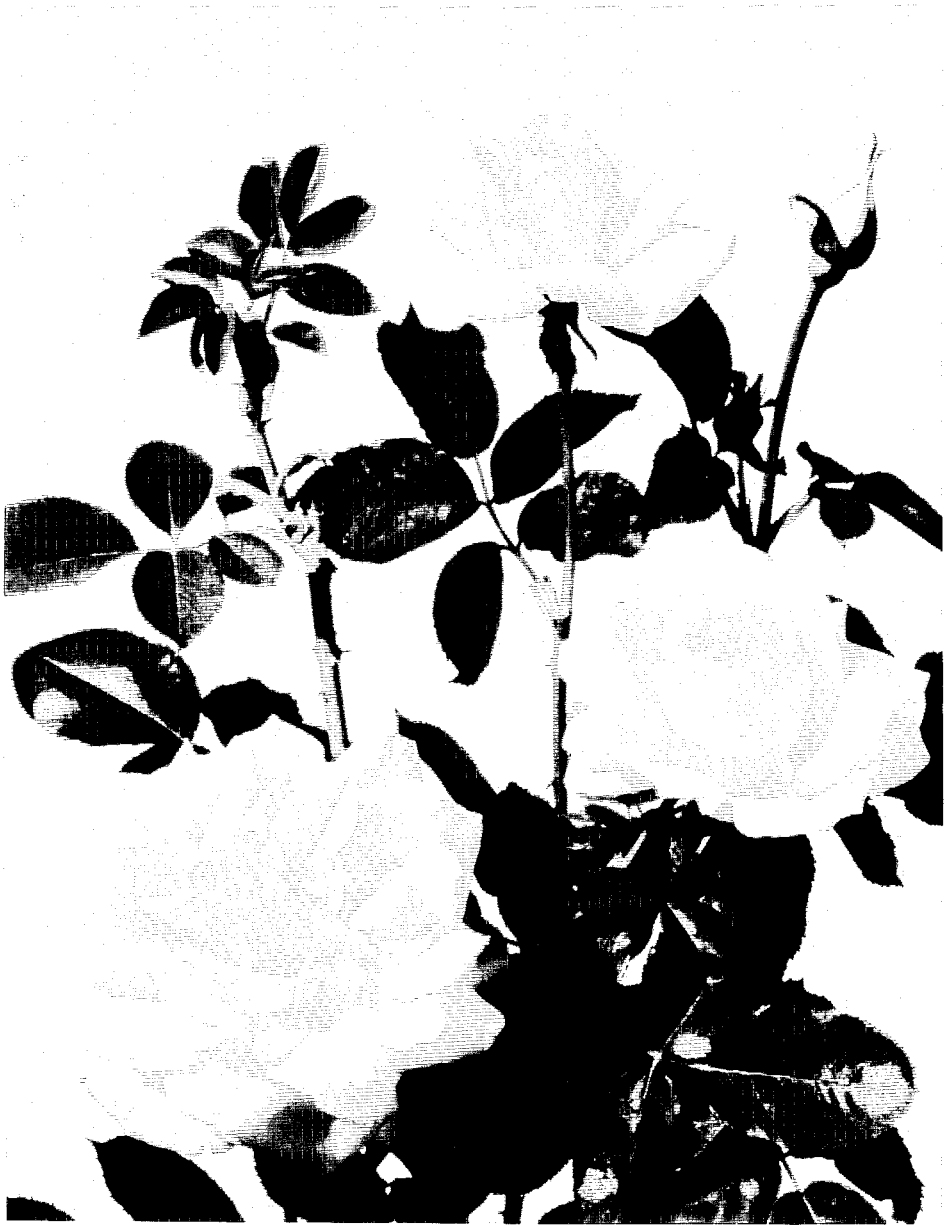
Inventor.
D. L. Armstrong
By: Cobb & Cobb
Attorneys.

United States Patent Office

Plant Pat. 2,914
Patented Aug. 5, 1969

2,914
ROSE PLANT

David L. Armstrong, Ontario, Calif., assignor to Armstrong Nurseries, Inc., Ontario, Calif., a corporation of California Filed Dec. 13, 1967, Ser. No. 690,363
Int. Cl. A01h 5/02
U.S. Cl. Plt.—18 1 Claim The present invention relates to a new and distinct variety of rose plant of the hybrid tea class, which was originated by me by crossing the rose variety known as "Helen Traubel" (Plant Patent No. 1,028) with the rose variety known as "Manitou" (unpatented), the former being the seed parent and the latter being the pollen parent.

The new variety resulted from an extensive breeding program conducted by me with the objective of producing improved hybrid tea rose varieties which bear flowers in the pink blend to red color range, and particularly combining with such flowers colors the flower size and form of the two parent varieties aforementioned, along with the greater flower petalage and attractive plant habit of "Manitou" and the vigor of "Helen Traubel." This new variety is one which achieves the aforementioned objective, as evidenced by the following unique combination of characteristics which are outstanding therein and which distinguish it from its parents, as well as from all other varieties of which I am aware:

(1) A vigorous plant having an attractive, upright-spreading, well-branched habit;

(2) Attractive, medium to large, semi-glossy foliage;

(3) A habit of usually bearing the flowers on medium to long, single stems of good strength;

(4) Double flowers of medium to large size, with an attractive urn-shaped bud form approaching that of the parent varieties, and with the open flowers being full-petaled and graceful;

(5) A distinctive and attractive light to medium pink blend flower color ranging between Azalea Pink and Carmine Rose, with some tinges of light yellow, particularly on the reverse side of the petals; and (6) A strong flower fragrance.

In comparison with its seed parent, "Helen Traubel," the new variety has a more compact plant habit, more flower petals, and a darker flower color tending more toward Carimne Rose than the flower color of this parent.

As compared with its pollen parent, "Manitou," which has a vigorous, bushy plant habit, with large, glossy foliage; flowers generally borne singly on strong stems of medium length, with the flowers being quite double in petalage and light to medium red in color and being particularly notable for its large flower size and attractive and graceful open-flower form, the new variety differs from this parent by bearing somewhat smaller flowers, more flower fragrance and a light pink blend flower color instead of the red flower color of this parent.

Asexual repoduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Bush; outdoors; seedling; for cut flowers and for garden decoration.
Class: Hybrid tea.
Breeding: Seedling.
*Seed parent.*—"Helen Traubel."
*Pollen parent.*—"Manitou."
Propagation: Holds its distinguishing characteristics through succeeding propagations by budding.

FLOWER

Locality where grown and observed: Ontario, Calif.
Flowers borne: Usually singly, but sometimes two or three to stem; in irregular clusters; on medium to long stems of normal strength.
Quantity of bloom: Free, outdoors.
Continuity: Nearly continuous during growing season.
Fragrance: Strong.
Bud:
*Peduncle.*—Average length; average caliper; erect; usually smooth; with several to many stipitate glands and none to few small prickles. Color—between Buffy Olive, Plate XXX (R) and Yellowish-Olive, Plate XXX (R).
*Before calyx breaks.*—Size—from medium to large. Form—from medium length to long; ovoid.
*As calyx breaks.*—Color—near Primrose Yellow, Plate 601/1, page 65 (W) overlaid with near Maize Yellow, Plate 607/2, page 69 (W) on area exposed longer to sun.
*Sepals.*—Usually with foliaceous appendages extending ¼ to ⅓ of sepal length. Inner surface—with fine, wooly tomentum. Outer surface—smooth. Alternate margins—lined with fine, wooly tomentum. Other margins—with several to many small stipitate glands and small, slender foliaceous parts.
*As first petal opens.*—Size—from average to large. Form—from medium length to long; ovoid; usually urn-shaped. Color: outside — between Chinese Coral, Plate 614/2, page 72 (W) and Azalea Pink, Plate 618/1, page 74 (W), blending with near Lemon Yellow, Plate 4/1, page 4 (W) toward base of petal; inside—between Chinese Coral, Plate 614/2, page 72 (W) and Azalea Pink, Plate 618/1, page 74 (W), blending with near Buttercup Yellow, Plate 5/1, page 5 (W) toward base of petal.
*Opening.*—Opens up well; is not retarded or prevented from opening by cold, hot, wet or dry weather.
Bloom:
*Size (when fully open).*—From average to large; from 4 inches to 5 inches.
*Petalage.*—Double; from 35 to 40 petals, plus 5 to 8 petaloids; arranged irregularly.
*Form.*—High-centered at first, but becoming cupped to high-centered; petals being at first tightly cupped, with tips reflexed outward, later becoming loosely cupped at maturity, with tips reflexed outward; outside petals of newly opened flower reflexed outward both along edges and apex, and intermediate petals of newly opened flower reflexed outward along apex; outside and intermediate petals of 3 days open flower reflexed outward both along edges and apex.
Petals:
*Texture.*—Medium thickness.
*Appearance.*—Inside—satiny. Outside—satiny.
*Shape.*—Outside—between round and broadly obovate, with apex flat and sometimes with 1 or 2 notches. Intermediate—obovate, with apex rounded and sometimes with 1 or 2 notches. Inside—narrowly obovate, with apex rounded and sometimes with 1 or 2 notches.

This description of a newly opened flower was made from a rose grown outdoors during the month of October at Ontario, Calif.

*Color.*—Outer petal: outside surface—near Azalea Pink, Plate618/2, page 74 (W), blending with near Lemon Yellow, Plate 4/2, page 4 (W) toward base of petal; inside surface—between Azalea Pink, Plate 618/2, page 74 (W) and Carmine Rose, Plate 621/2, page 75 (W), blending with near Aureolin, Plate 3/1, page 3 (W) toward base of petal. Intermediate petal: outside surface—between Azalea Pink, Plate 618/1, page 74 (W) and Azalea Pink, Plate 618/2, page 74 (W), blending with near Lemon Yellow, Plate 4/2, page 4 (W) toward base of petal; inside surface—between Azalea Pink, Plate 618/2, page 74 (W) and Carmine Rose, Plate 621/1, page 75 (W), blending with near Aureolin, Plate 3/1, page 3 (W) toward base of petal. Inner petal: outside surface—between Azalea Pink, Plate 618/1, page 74 (W) and Azalea Pink, Plate 618/2, page 74 (W), blending with near Lemon Yellow, Plate 4/2, page 4 (W) toward base of petal; inside surface—between Azalea Pink, Plate 618/2, page 74 (W) and Carmine Rose, Plate 621/1, page 75 (W), blending with near Aureolin, Plate 3/1, page 3 (W) toward base of petal.

This description was made from a rose that was open for three days outdoors during the month of October at Ontario, Calif.

*Color.*—Outer petal: outside surface—between Carmine Rose, Plate 621/3, page 75 (W) and Dawn Pink, Plate 525/3, page 137 (W), blending with near Aureolin, Plate 3/2, page 3 (W) toward base of petal; inside surface—between Carmine Rose, Plate 621/3, page 75 (W) and Rhodamine Pink, Plate 527–2, page 138 (W), blending with near Aureolin, Plate 3/2, page 3 (W) toward base of petal. Inner petal: outside surface—between Carmine Rose, Plate 621/2, page 75 (W) and Rhodamine Pink, Plate 527/2, page 138 (W), blending with near Aureolin, Plate 3/2, page 3 (W) toward base of petal; inside surface—between Phlox Pink, Plate 625/2, page 77 (W) and Rhodamine Pink, Plate 527/1, page 138 (W), blending with near Aureolin, Plate 3/2, page 3 (W) toward base of petal.

*General color effect.*— Newly opened flower—between Azalea Pink, Plate 618/2, page 74 (W) and Carmine Rose, Plate 621/1, page 75 (W). Three days open—between Carmine Rose, Plate 621/1, page 75 (W) and Rhodamine Pink, Plate 527/1, page 138 (W).

*Behavior.*—Drop off cleanly; not particularly affected by cold, hot, wet or dry weather.

*Flower longevity.*—On bush in garden—2 or 3 days in October. Cut roses grown outdoors and kept at living-room temperatures—from 2 to 5 days in October.

REPRODUCTIVE ORGANS

Stamens: Average number; arranged regularly about pistils; a few mixed with petaloids.

Filaments: From short to medium length (from 4 mm. to 12 mm. long); most with anthers. Color—near Indian Yellow, Plate 6/1, page 6 (W).

Anthers: Medium size; all open approximately at once. Color: upper side—margins near Saffron Yellow, Plate 7/1, page 7 (W), with remainder near Aureolin, Plate 3/2, page 3 (W); under side—margins near Saffron Yellow, Plate 7/1, page 7 (W), with remainder near Aureolin, Plate 3/2, page 3 (W).

Pollen: Moderate abundance. Color—near Tangerine Orange, Plate 9/2, page 9 (W).

Pistils: Average number (approximately 75 in number).

Styles: Uneven; from short to average length; thin; bunched. Color—upper ½ of style near Crimson, Plate 22/1, page 22 (W), with remainder near Empire Yellow, Plate 603/1, page 66 (W).

Stigma: Color—near Egyptian Buff, Plate 407/1, page 122 (W).

Ovaries: Usually all enclosed in calyx.

Hips: Average length; globular; smooth; walls thick and fleshy. Color (½ mature)—near Yellow Ochre, Plate XV (R).

Sepals: Falling soon; from short to medium length. Color: inside—near Deep Olive-Buff, Plate XL (R); outside near Citron Green, Plate XXXI (R).

Seeds: Few (from 10 to 15 in number); medium size.

PLANT

Foilage:

*Leaves.*—Compound of usually 3–7 leaflets; abundant; from medium to large size; somewhat leathery; semi-glossy.

*Leaflets.*—Shape—oval. Apel—acute. Base—round. Margin—simply serrate.

*Color.*—Mature: upper surface— between Dark Dull Yellow Green, Plate XXXII (R) and Empire Green, Plate XXXII (R); under surface—near Chromium Green, Plate XXXII (R). Young: upper surface—near Dark Cress Green, Plate XXXI (R); under surface between Olive-Brown, Plate XL (R) and Deep Olive, Plate XL (R).

*Rachis (the supporting stem of the compound leaf).*—Average size. Upper side—grooved; with few to several small stipitate glands on edges. Under side—moderately smooth; with stipitate glands and none to few small prickles.

*Stipules.*—From short to medium length; from medium width to wide; with short points turning out at an angle of less than 45°.

*Disease resistance.*—Better than average resistance to mildew, as determined by comparison with other varieties grown under comparable conditions at Ontario, Calif.

Growth:

*Habit.*—Upright-spreading; much-branched.

*Growth.*—Vigorous.

*Canes.*—From medium caliper to heavy.

*Main stems.*—Color—near Grape Green, Plate XLI (R). Large prickles—several; from short to medium length; hooked slightly downward; with medium length, narrow base; color—near Sorghum Brown, Plate XXXIX (R). Small prickles—from none to few; color—near Sorghum Brown, Plate XXXIX (R). Hairs—none.

*Branches.*—Color—near Rainette Green, Plate XXXI (R). Large prickles—several; from short to medium length; hooked slightly downward; with medium length, narrow base; color—near Cacao Brown, Plate XXVIII (R). Small prickles—few; color—near Cacao Brown, Plate XXVIII (R). Hairs—none.

*New shoots.*—Color—near Deep Chrysolite Green, Plate XXXI (R), overlaid with near Citrine Drab, Plate XL (R) on side exposed to the sun. Large prickles—several; from short to medium length; hooked slightly downward; with medium length, narrow base; color—near Prussian Red, Plate XXVII (R). Small prickles—few; color—near Prussian Red, Plate XXVII (R). Hairs—none.

I claim:

1. A new and distinct variety of rose plant of the hybrid tea class, substantially as herein shown and described, characterized particularly as to novelty by the unique combination of a vigorous plant having an attractive, upright-spreading, well-branched habit, attractive, medium to large, semi-glossy foliage, a habit of usually bearing the flowers on medium to long, single stems of good strength, double flowers of medium to large size, with an attractive urn-shaped bud form approaching that of the parent varieties, and with the open flowers being full-petaled and graceful, a distinctive and attractive light to medium pink blend flower color ranging between Azalea Pink and Carmine Rose, with some tinges of light yellow, particularly on the reverse side of the petals and a strong flower fragrance.

No references cited.

ROBERT E. BAGWILL, Primary Examiner